(12) United States Patent
Schöning

(10) Patent No.: US 9,245,494 B2
(45) Date of Patent: Jan. 26, 2016

(54) COLORBLIND ACCESSIBILITY TEST FOR CORRESPONDING SCREEN DISPLAYS

(71) Applicant: Software AG, Darmstadt (DE)

(72) Inventor: Harald Schöning, Dieburg (DE)

(73) Assignee: SOFTWARE AG, Darmstadt (DE)

( * ) Notice: Subject to any disclaimer, the term of this patent is extended or adjusted under 35 U.S.C. 154(b) by 260 days.

(21) Appl. No.: 14/073,785

(22) Filed: Nov. 6, 2013

(65) Prior Publication Data

US 2015/0123983 A1    May 7, 2015

(51) Int. Cl.
  G09G 5/02    (2006.01)
  G06T 11/00    (2006.01)
  G09G 5/30    (2006.01)

(52) U.S. Cl.
  CPC ............... *G09G 5/02* (2013.01); *G06T 11/001* (2013.01); *G09G 5/30* (2013.01)

(58) Field of Classification Search
  None
  See application file for complete search history.

(56) References Cited

U.S. PATENT DOCUMENTS

| | | | |
|---|---|---|---|
| 5,467,123 A | 11/1995 | Zeevi et al. | |
| 7,124,375 B1 | 10/2006 | Steele et al. | |
| 7,344,250 B2 | 3/2008 | Sato | |
| 7,983,920 B2 | 7/2011 | Sinclair, II | |
| 8,169,447 B2 | 5/2012 | Bhogal et al. | |
| 8,412,694 B2 | 4/2013 | Wang et al. | |
| 2012/0121172 A1* | 5/2012 | Wang | G06K 9/036 382/165 |
| 2014/0380154 A1* | 12/2014 | Solcz | G06T 11/001 715/256 |
| 2015/0205882 A1* | 7/2015 | Vukas | G06F 17/30256 707/758 |

OTHER PUBLICATIONS

AccessColor-Online Tool for Colour Contrast, Feb. 4, 2013, 2 pages. https://web.archive.org/web/20130204074748/http://www.accesskeys.org/tools/color-contrast.html.
About EXSYST, retrieved Sep. 24, 2015, 1 page. https://web.archive.org/web/20121208044119/http://www.exsyst.org/.
Guitar Home Page, Oct. 16, 2012, 6 pages. https://web.archive.org/web/20121016192735/http:/sourceforge.net/apps/mediawiki/guitar/index.php?title=GUITAR_Home_Page.
GSA Image Analyser, Oct. 22, 2012, 3 pages. https://web.archive.org/web/20121022134526/http:/image.analyser.gsa-online.de/?lang=en.

(Continued)

*Primary Examiner* — Kee M Tung
*Assistant Examiner* — Ryan D McCulley
(74) *Attorney, Agent, or Firm* — Nixon & Vanderhye PC

(57) ABSTRACT

A method and apparatus that are capable of identifying corresponding screen displays that convey color coded information and identifying whether color coded information found in corresponding screen displays is likely to be accessible or inaccessible to a colorblind individual. The method and apparatus are capable of receiving data corresponding to a plurality of screen displays including information encoded in color. The method and apparatus are capable of identifying corresponding screen displays from the plurality of screen displays. The method and apparatus are further capable of detecting text and color encoded information that are different in the first and second corresponding screen displays at first and second locations, respectively. The method and apparatus are further capable of determining a proximity of the first and the second locations when there is text that is different in the first and second corresponding screens at the first location, and generating a colorblindness accessibility indicator based on whether text that is different was detected/ and or the determined proximity.

18 Claims, 17 Drawing Sheets
(14 of 17 Drawing Sheet(s) Filed in Color)

(56) References Cited

OTHER PUBLICATIONS

Wave, Feb. 1, 2013, 2 pages. https://web.archive.org/web/20130201100704/http:/wave.webaim.org/.

Colorblind_Web_Page_Filter, Feb. 4, 2012, 2 pages. https://web.archive.org/web/20120204095616/http:/colorfilter.wickline.org/.

Coblis-Color Blindness Simulator, Apr. 27, 2013, 12 pages. https://web.archive.org/web/20130427000034/http:/www.color-blindness.com/coblis-color-blindness-simulator.

Accessibility Color Wheel, Jan. 21, 2013, 2 pages. https://web.archive.org/web/20130121012348/http:/gmazzocato.altervista.org/colorwheel/wheel.php.

PAX-it! Image Analysis Software, Jan. 26, 2013, 2 pages. https://web.archive.org/web/20130126151817/http:/www.paxit.com/paxit/enhanced.asp.

Juicy Studio Colour Contrast Analyser, Sep. 5, 2008, 2 pages. https://web.archive.org/web/20080905223524/http:/www.juicystudio.com/services/colourcontrast.asp.

* cited by examiner

705b → Password: *******

Six-character minimum with no spaces
Learn how to create a strong, memorable password.

710b → Password strength:

COLORBLIND ACCESSIBILITY TEST FOR CORRESPONDING SCREEN DISPLAYS

CROSS-REFERENCE TO RELATED APPLICATIONS

This application is related to U.S. application Ser. No. 14/073,781, entitled "Colorblind Accessibility Test for a Screen Display," by Dr. Harald Schöning, filed on Nov. 6, 2013, which is incorporated by reference herein in its entirety.

BACKGROUND

Colorblindness, or the inability or decreased ability to see color, affects a significant percentage of the population. However, among people afflicted with colorblindness, people can be affected to varying degrees and there is no uniform set of colors that can be distinguished by every colorblind individual. As a result, using only color graphics to convey information in a computer application, such as an operating system, web page, or graphic display, can make this information inaccessible to certain colorblind individuals. Developers of screen displays who might have perfect color sight, however, are often unaware that they have included color coded information that is inaccessible to colorblind individuals. Further, by analyzing a single instance of a single screen display it might not be apparent that color is being used to convey information. The prevalence of this problem is significant enough that the federal government has defined regulations requiring that certain computer systems must be accessible to colorblind people (e.g., Section 508 of the Rehabilitation Act Amendments of 1998).

SUMMARY

The disclosed subject matter can include a method for testing corresponding screen displays for colorblind accessibility. The method can include receiving, at a processor, data corresponding to a plurality of screen displays including information encoded in color. The method can further include identifying first and second corresponding screen displays from the plurality of screen displays using the processor. The method can further include detecting whether any text is different in the first and second corresponding screen displays at a first location using the processor. The method can further include detecting color encoded information that is different in the first and second corresponding screen displays at a second location using the processor. The method can further include determining a proximity of the first and the second locations when there is text that is different in the first and second corresponding screen displays at the first location, and generating a colorblindness accessibility indicator based on whether text that is different was detected and/or the determined proximity using the processor.

Embodiments of the disclosed subject matter can provide one or more of the following capabilities. Embodiments of the disclosed subject matter can be capable of identifying corresponding screen displays that convey color coded information. Embodiments of the disclosed subject matter can be capable of identifying whether color coded information found in corresponding screen displays is likely to be accessible or inaccessible to a colorblind individual. Embodiments of the disclosed subject matter can automatically add text to color coded information to make the information more accessible to a colorblind individual. Embodiments of the disclosed subject matter can provide an editing unit to allow a user to manually input text in proximity to the color coded information to make the information accessible to a colorblind individual. Embodiments of the disclosed subject matter can generate a positive indicator if corresponding screen displays are likely to be accessible to colorblind people or a negative indicator if corresponding screen displays are likely to be inaccessible to colorblind people. Embodiments of the disclosed subject matter can display a positive or negative indicator denoting whether the corresponding screen displays have passed or failed the accessibility test to users who are colorblind.

These and other capabilities of the disclosed subject matter will be more fully understood after a review of the following figures, detailed description, and claims.

BRIEF DESCRIPTION OF THE FIGURES

The patent or application file contains at least one drawing executed in color. Copies of this patent or patent application publication with color drawing(s) will be provided by the Office upon request and payment of the necessary fee.

DETAILED DESCRIPTION

Embodiments of the disclosed subject matter disclosed herein can provide techniques for tracking different instances of a screen display (also referred to herein as "screens") to determine if it uses color to convey information. Information that is conveyed only in color might not be accessible to people who are colorblind. For example, some colorblind people cannot distinguish between red and green. Accordingly, if a screen display conveys information using red or green (e.g., a red or green circle in a screen display), and does not include any additional text describing the information represented by the color, then this information might not be accessible to some colorblind people. Because of this use of color in different instances of a screen, if a testing algorithm analyzes only a single instance of a screen it may not be apparent that color is being used to convey information.

Thus, a computer system can detect two or more instances of a screen that correspond to each other. Corresponding instances of a screen (also referred to herein as "corresponding screens") can have similar layouts and contain all, or almost all of the same elements, including graphics and text. Corresponding screens can also include some different elements (e.g., different color coded information and/or different text associated with color coded information). The corresponding screens can then be tested to determine whether they include color coded information and whether that color coded information varies. Based on this analysis, the computer can be configured to generate a positive indicator if the corresponding screens are likely to be accessible to colorblind people or a negative indicator if the corresponding screens are likely to be inaccessible to colorblind people. The computer can also be configured to display the positive or negative indicator denoting whether the correspond screens have passed or failed the accessibility test to users who are colorblind. Other embodiments are within the scope of the disclosed subject matter.

Figure 1A:
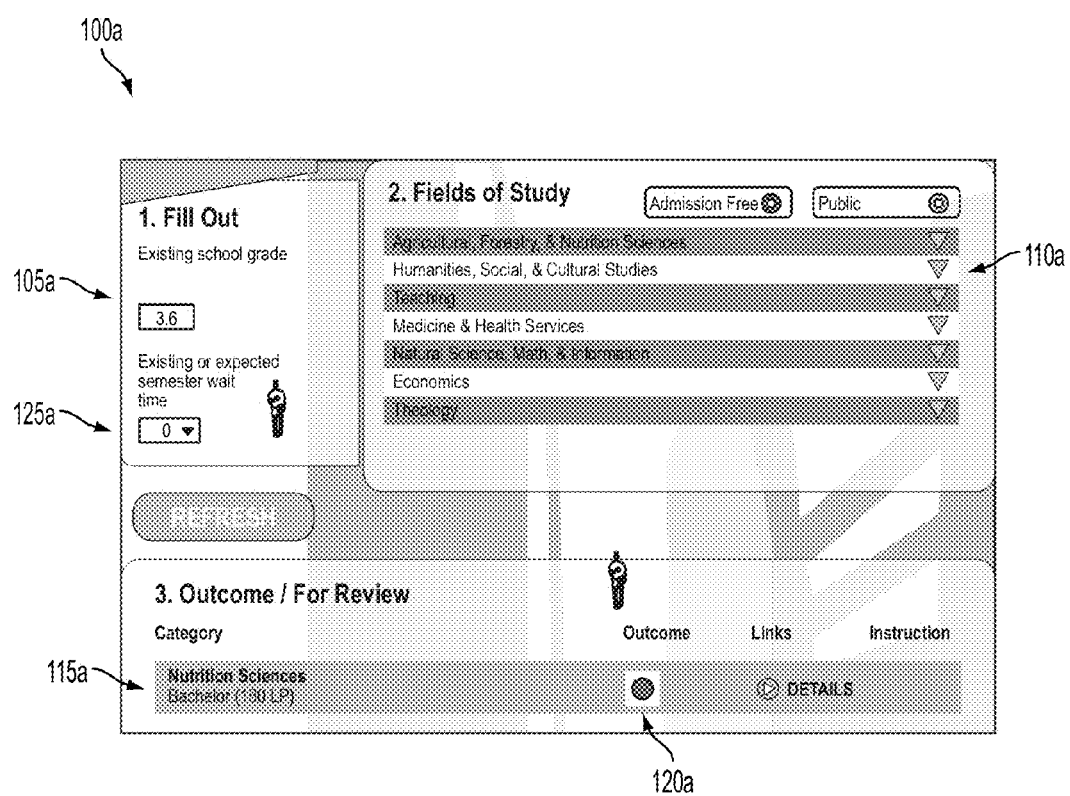
FIGS. 1a, 1b, 1c and 1d are exemplary screen displays including color to convey information to a user.
Figure 1B:
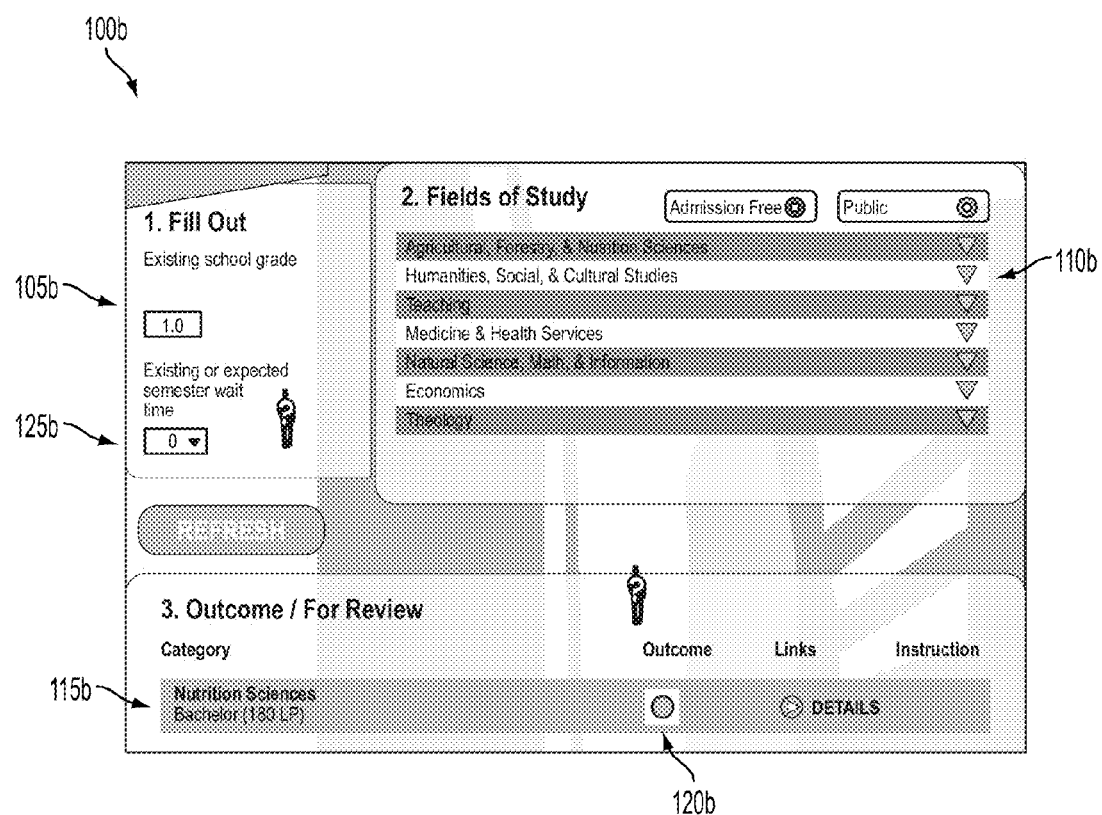

FIGS. 1a and 1b illustrate a pair of exemplary instances of a screen 100a and 100b (also referred to as screens 100a and 100b herein) that conveys color coded information. While the color coded information contained within the corresponding screens 100a and 100b might not be detected when analyzing each screen in isolation, the color coded information is more likely to be detected when comparing the corresponding screens 100a and 100b. For example, the nearly identical screens 100a and 100b can include fields 105a and 105b that display an overall grade achieved from a secondary school (which can be provided by a user or an external system), fields 125a and 125b that display a semester wait time completed or to be completed (which can be provided by a user or an external system), fields 110a and 110b that display a list of areas of study, fields 115a and 115b that display a particular area of study selected by a user, and circles 120a and 120b that use color to indicate likelihood of admission to a particular area of study based on a student's overall grade and semester wait time (e.g., the circle can appear in green if based on a student's overall grade and/or semester wait time a student is likely to gain admission to a particular area of study, or it can appear in red if based on a student's overall grade and/or semester wait time a student is unlikely to gain admission to a particular area of study).

In FIG. 1a, the student's overall grade is 3.6 and in FIG. 1b, the student's overall grade is 1.0 (the grade scale is from 1.0 to 4.0, 1.0 being the best grade that a student can achieve and 4.0 being the worst grade). In FIG. 1a, the circle 120a is red indicating that a grade of 3.6 is unlikely for admission, while in FIG. 1b, the circle 120b is green indicating that a grade of 1.0 is likely for admission. Further, the semester wait times in both FIGS. 1a and 1b are 0 (a longer wait time can improve a student's likelihood for admission). The screens 100a and 100b correspond to each other in that they both display areas of study and convey likelihood of admission to an area of study based on a student's overall grade and/or semester wait time (e.g., both screens include the same underlying structure and form, but with different content). While screens 100a and 100b might correspond to each other, they contain different overall grades, as shown in fields 105a and 105b, and different color coded information, as shown in circles 120a and 120b. An algorithm testing for colorblind accessibility that is applied to screens 100a or 100b in isolation (e.g., analyzing one instance without considering the other) might not detect that the red colored circle 120a or the green colored circle 120b convey likelihood of admission. On the other hand, an algorithm testing for colorblind accessibility that compares screens 100a and 100b can detect the different overall grades in fields 110a and 110b, as well as the different colored circles 120a and 120b. Thus, the algorithm can detect that color is being used to convey information. As will be described in connection with the exemplary embodiments discussed below, the color coded information contained within corresponding screens 100a and 100b can be further tested for its accessibility to colorblind people.

Figure 1C:
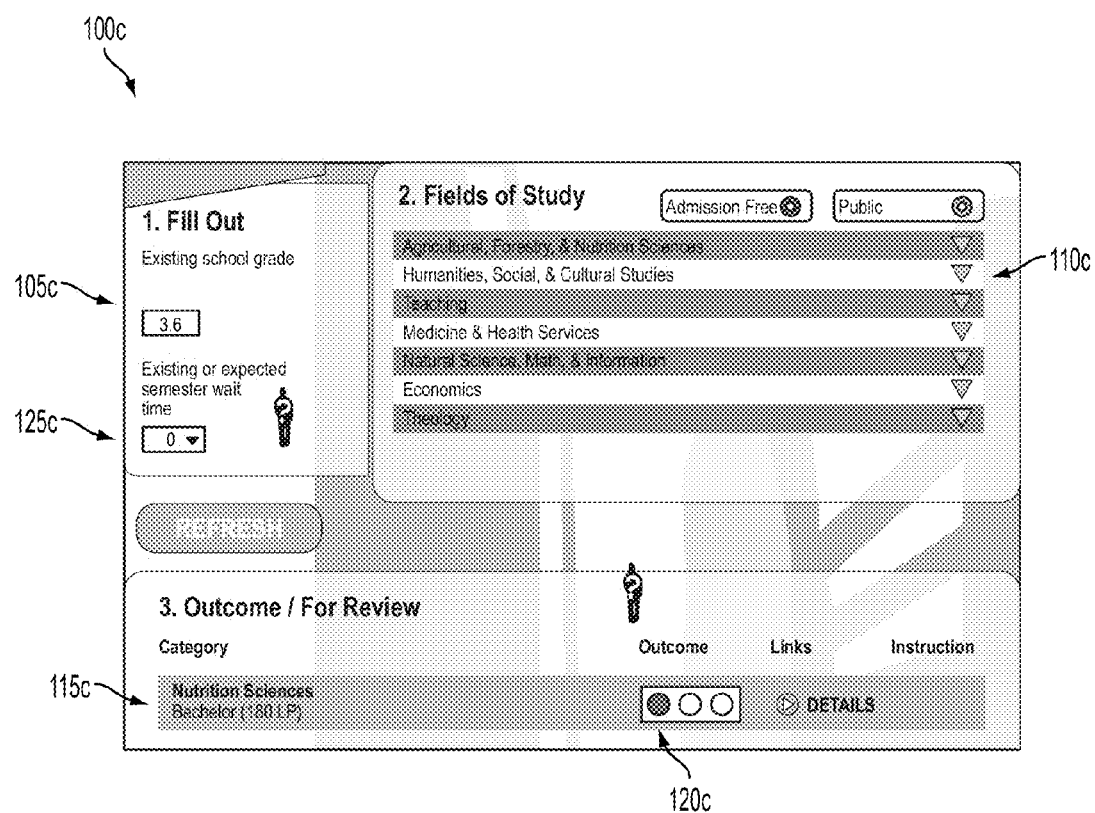
Figure 1D:
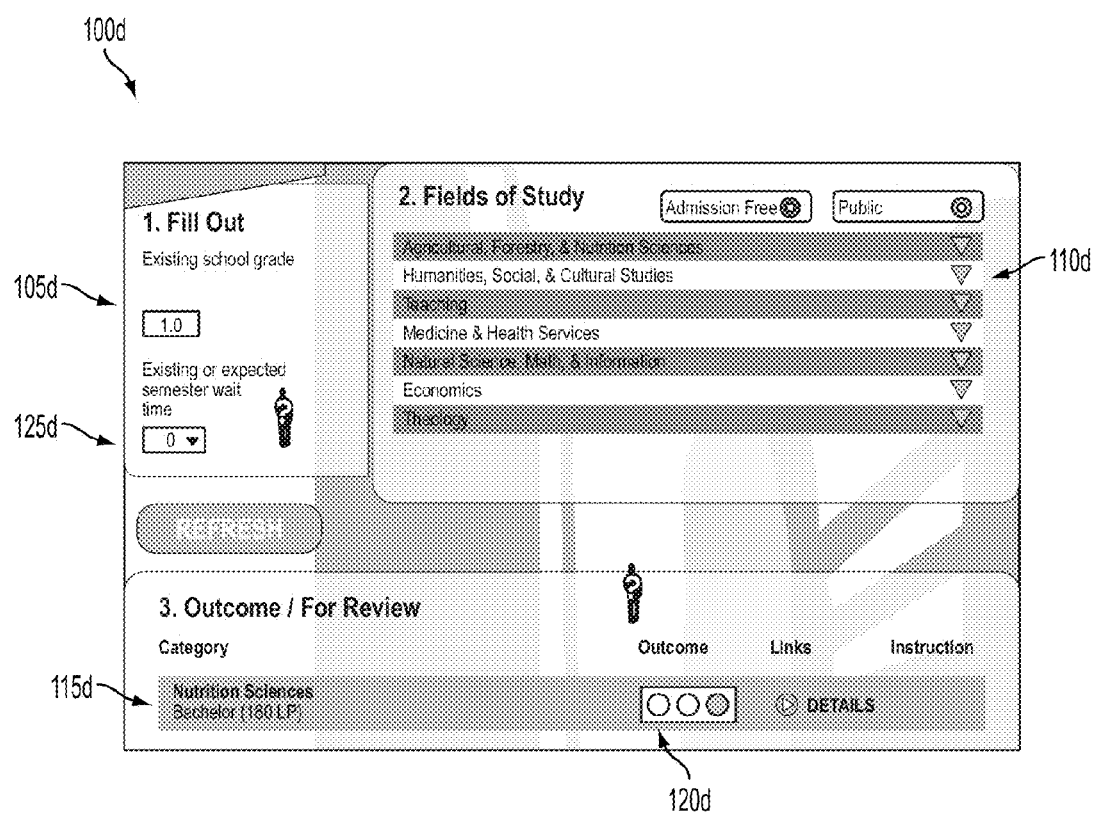

A further example of different instances of a screen that can be analyzed by embodiments of the subject matter disclosed herein include a color display (e.g., a traffic light) that can show different colors under different situations. For example, a screen can include a traffic light color display (either vertical or horizontal) that displays "red" under one set of conditions, "yellow," under a second set of conditions and "green" under a third set of conditions (e.g., all at different times). For example, FIGS. 1c and 1d convey the same information as depicted in FIGS. 1a and 1b, respectively, except the color coded information in fields 120c and 120d shown in FIGS. 1c and 1d are displayed in a horizontal "traffic light configuration." An algorithm testing for colorblind accessibility that is applied to different instances of a screen display including a traffic light color display can detect that the different colors of the display appear under different sets of conditions. As will be described in connection with the exemplary embodiments discussed below, the color coded information in the screens including a traffic light (or another color display) can be further tested for its accessibility to colorblind people.

Figure 2A:
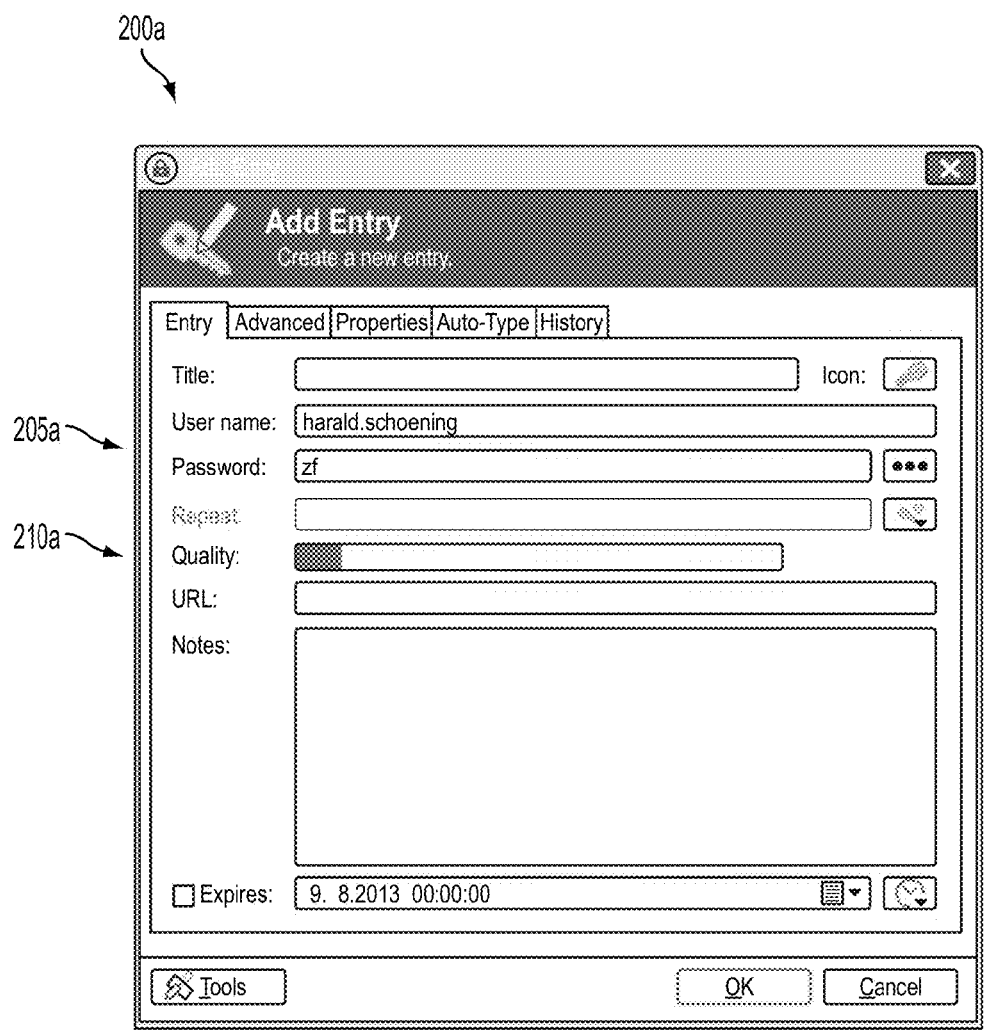
FIGS. 2a, 2b, 2c and 2d are exemplary screen displays including color to convey information to a user.
Figure 2B:
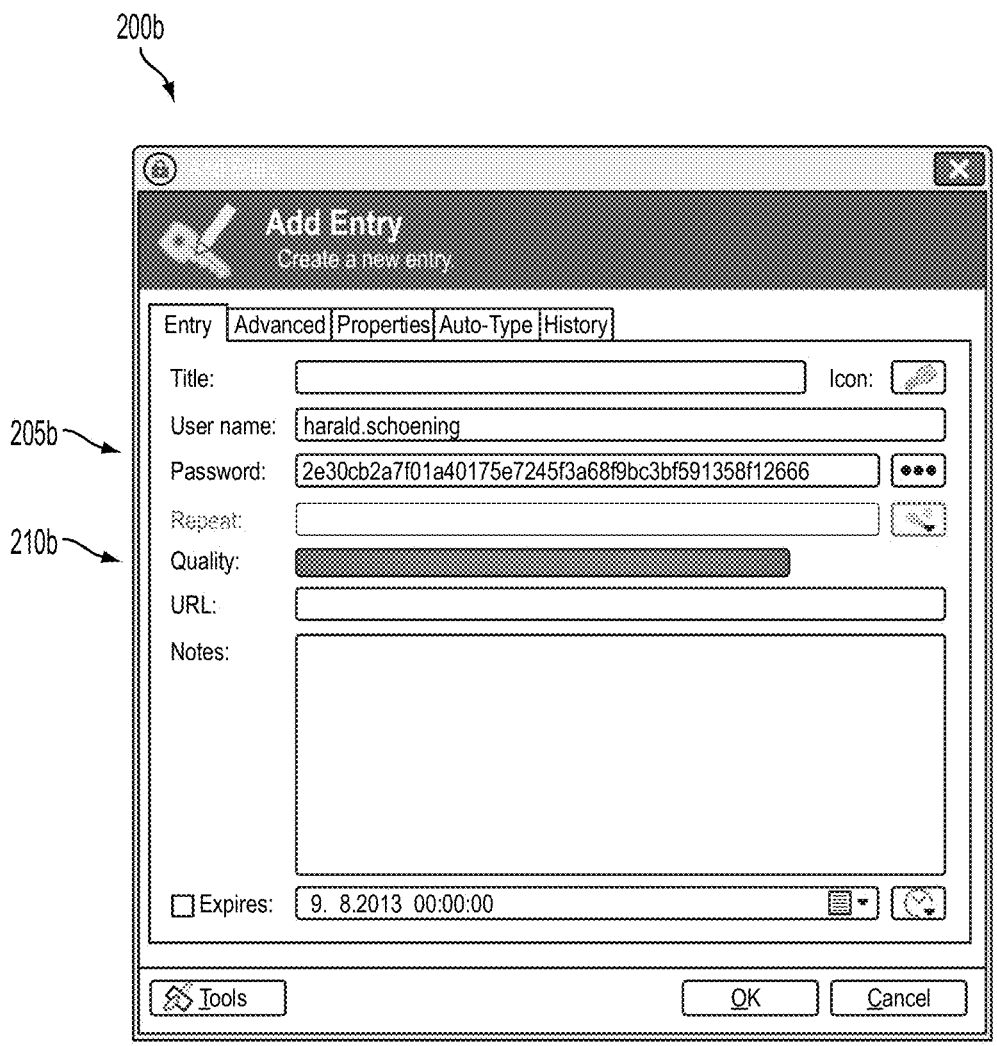
Figure 2C:
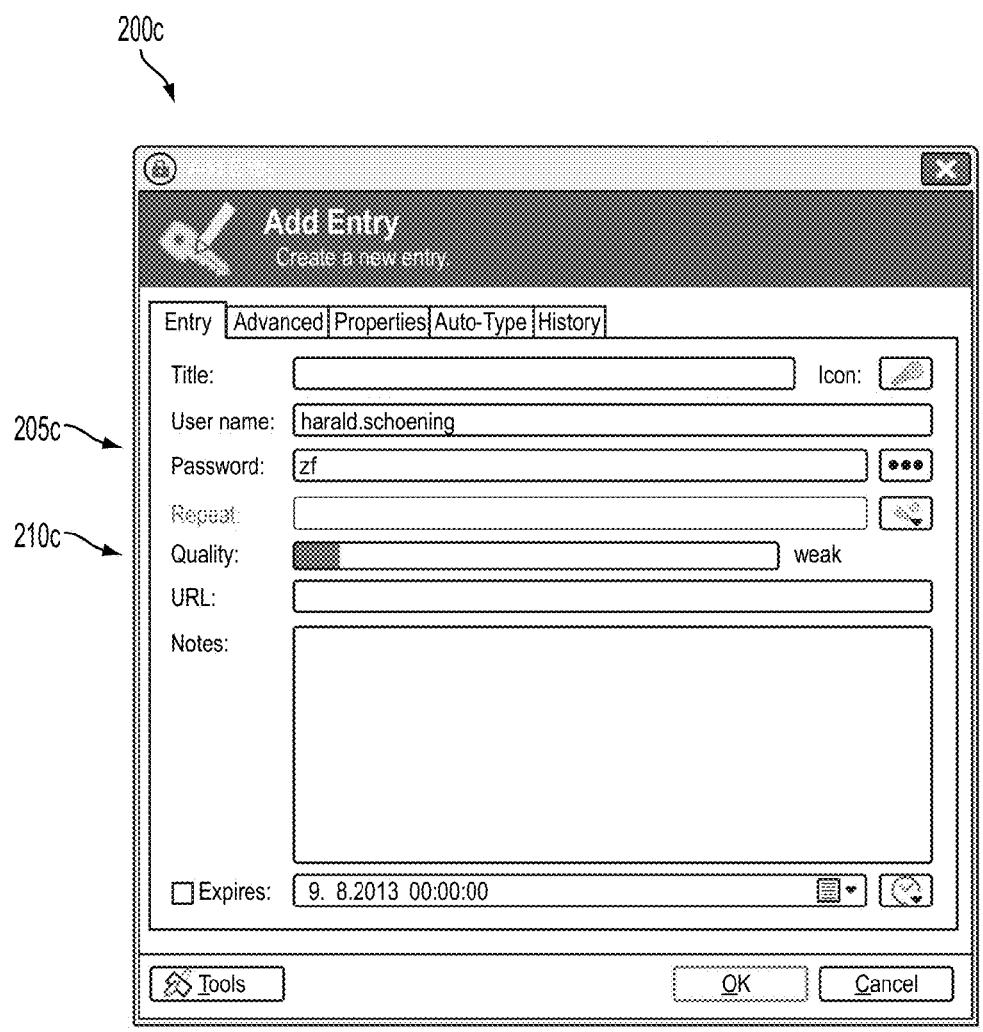
Figure 2D:
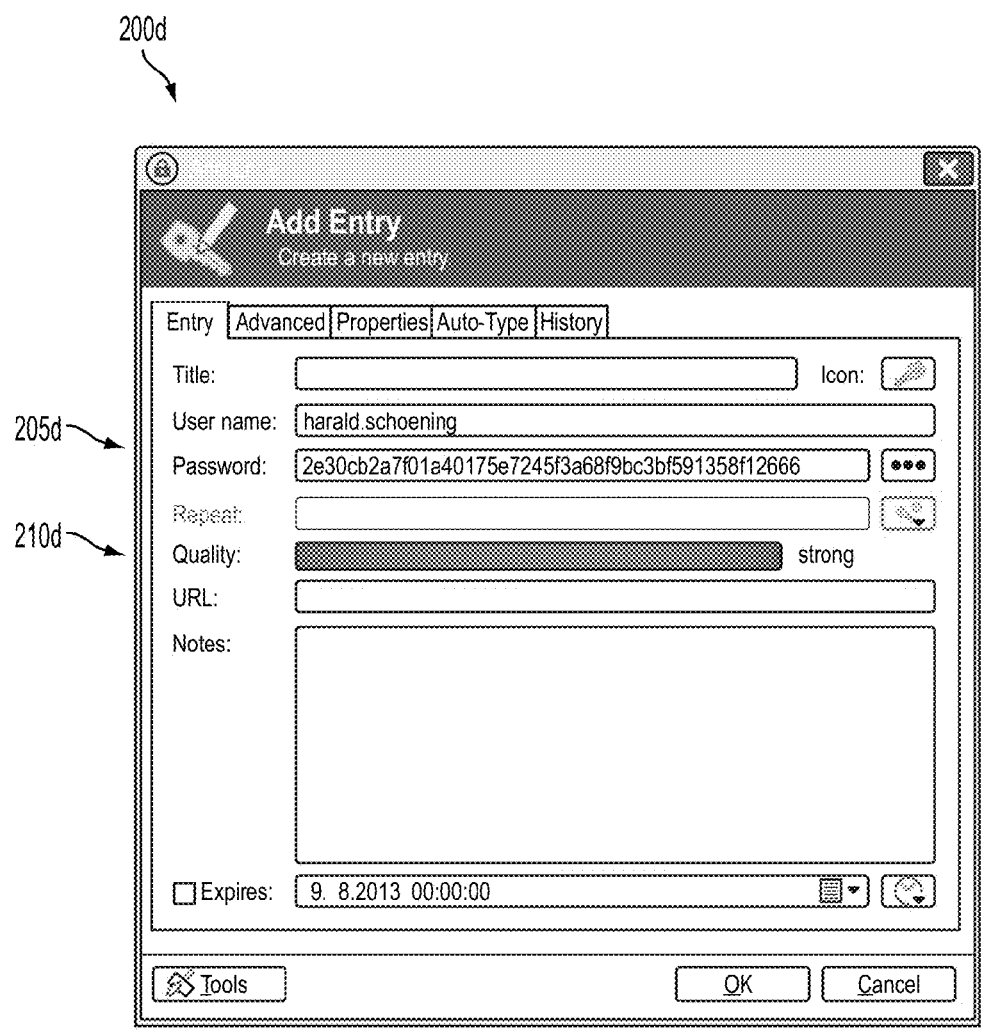
Figure 3:
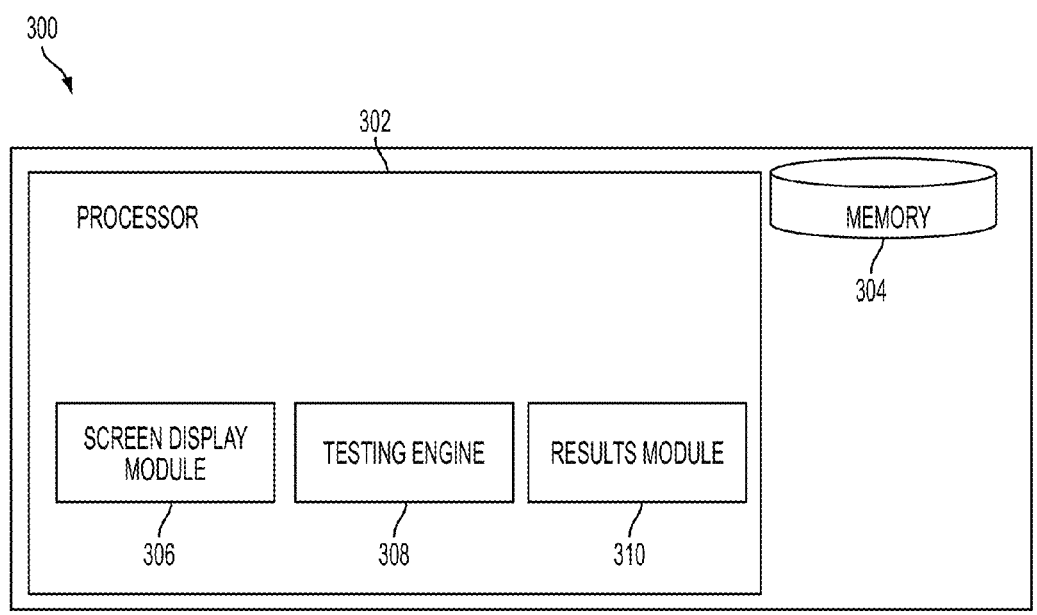
FIG. 3 is a schematic diagram of a computer system for testing graphics conveying information using color.

The exemplary screen displays illustrated in FIGS. 2a and 2b are further examples of different instances of a screen that can be analyzed by embodiments of the subject matter disclosed herein. Based on a user's interaction with instances 200a and 200b (also referred to herein as screens 200a and 200b) of a display, different color coded information can appear. For example, in FIG. 2a, two characters have been entered into the "Password" field 205a of screen display 200a, and the colored bar indicator in the "Quality" field 210a displays the color orange, denoting a weak password. In FIG. 2b, which illustrates a different instance of the same screen display shown in FIG. 2a, many characters have been entered into the "Password" field 205b, and the colored bar indicator in the "Quality" field 210b displays a change in color from orange to green, indicating a strong password. Accordingly, screens 200a and 200b correspond to each other because they are different instances of the same screen even though they contain different entries in the "Password" field and different color coded information in the "Quality" field. An algorithm testing for colorblind accessibility that is applied to screens 200a or 200b in isolation (e.g., analyzing one instance without considering the other) might not detect that the colored bar indicators in the "Quality" fields 210a and 210b convey password strength. On the other hand, an algorithm testing for colorblind accessibility that compares screens 200a and 200b can detect that the different colors of the bar indicators in "Quality" fields 210 and 210b convey password strength. In contrast to FIGS. 2a and 2b, FIGS. 2c and 2d convey the same information as depicted in FIGS. 2a and 2b, respectively. However, the "Quality" fields 210c and 210d shown in FIGS. 2c and 2d include text, in addition to colored bar indicators, that conveys the strength of the password (e.g., "weak" and "strong"). As will be described in connection with the exemplary embodiments discussed below, the color coded information in corresponding screens 200a and 200b, and corresponding screens 200c and 200d can be further tested for its accessibility to colorblind people. FIG. 3 is a block diagram of an exemplary computing system 300 that can be used to test for corresponding screens that use color coded information and/or to test corresponding screens for accessibility to colorblind people. Computing system 300 preferably includes a processor 302, a memory 304, a screen display module 306, a testing engine 308 for testing colorblind accessibility, and a results module 310 for displaying the outcome of the colorblind accessibility test. While each of the foregoing components are shown as specific blocks in FIG. 3, this is exemplary only. Although the screen display module 306, testing engine 308 and results module 310 are shown in FIG. 3 as part of processor 302, this is not required. The functionality described herein can be combined into a single component or spread across several components.

The computing system 300 can be configured to analyze instances of screens that may contain graphics. Examples of screen displays containing graphics include user interfaces, operating systems, webpages, PowerPoint® presentations, and Excel® spreadsheets, although the system 300 can be used with virtually any device capable of displaying information (e.g., televisions, computer screens, game console displays, smartphone screens, tablet screens, airport check-in kiosks). In some embodiments, the techniques described herein can be used with physical printouts (e.g., by digitizing them using a scanner and/or camera). For example, pages of a book can be digitized using a scanner so that they can be analyzed by the techniques described herein. The computing system 300 can be a standalone system that is implemented on dedicated hardware, can be software as a service, and/or can be a stand-alone application (e.g., an application for an iPad®).

The processor 302 can be a general-purpose device, such as a microcontroller and/or a microprocessor, such the Pentium IV series of microprocessor manufactured by the Intel Corporation of Santa Clara, Calif., specially programmed to provide the functionality described herein. In certain embodiments, the processor can be a dedicated purpose device, such as an Application Specific Integrated Circuit (ASIC) or a Field Programmable Gate Array (FPGA) that has been designed to implement in its hardware and/or firmware at least a part of an embodiment disclosed herein.

The memory 304 can be an apparatus capable of storing analog or digital information, such as instructions and/or data. Examples include a nonvolatile memory, volatile memory, Random Access Memory, RAM, Read Only Memory, ROM, flash memory, magnetic media, a hard disk, a floppy disk, a magnetic tape, an optical media, an optical disk, a compact disk, a CD, a digital versatile disk, a DVD, and/or a raid array, etc. The memory 304 can be coupled to a processor and/or can store instructions adapted to be executed by the processor, such as according to an embodiment disclosed herein.

The screen display module 306 can be configured to provide screen displays containing graphics with color coded information to a display (not shown) such that the screen displays are shown to a user. The display module 306 can also be configured to provide the screen displays to the testing engine 308, either directly and/or via a network. A network can be and/or utilize any of a wide variety of sub-networks, such as a circuit switched, public-switched, packet switched, data, telephone, telecommunications, video distribution, cable, terrestrial, broadcast, satellite, broadband, corporate, global, national, regional, wide area, backbone, packet-switched TCP/IP, Fast Ethernet, Token Ring, public Internet, private, ATM, multi-domain, and/or multi-zone sub-network, one or more Internet service providers, and/or one or more information devices, such as a switch, router, and/or gateway not directly connected to a local area network, etc.

The testing engine 308 can be configured to receive data corresponding to the screen displays from the screen display module 306 and test them to determine how accessible they are likely to be to a colorblind individual (as described more fully below). While an exemplary embodiment of the testing engine 308 receives screen displays from the screen display module 306, other configurations are possible. For example, the testing engine 308 can be configured as part of the screen display module 306 itself. Further, the testing engine 308 can be configured to check for instances of corresponding screen displays. The testing engine 308 can also be configured to identify identical text in corresponding screens and remove or hide any identical text found. The testing engine 308 can further be configured to analyze screen displays for color differences that convey color coded information.

The testing engine 308 can further be configured to detect whether there is text associated with color coded information included in the corresponding screens. The testing engine 308 can also be configured to evaluate the text and to determine whether or not the text describes what the color coded information represents. The testing engine 308 can further be configured to generate a positive indicator if the color coded information found in the corresponding screens includes text that describes what the color coded information represents (e.g., is likely to be accessible to a colorblind individual). The testing engine 308 can be configured to generate a negative indicator if the color coded information found in the corresponding screens does not include text or does not include text that describes what the color coded information represents (e.g., is not likely to be accessible to a colorblind individual). The testing engine 308 can be further configured to generate a negative or positive indicator based on whether the color coded information found in the corresponding screens is in compliance with federal government regulations defining accessibility of screens to colorblind people (e.g., Section 508 of the Rehabilitation Act Amendments of 1998).

The testing engine 308 can also be configured to communicate results (e.g., a positive or negative indicator) to a results module 310, via, for example, a network connection (e.g., the Internet, intranet, and/or a local area network) or an internal bus. The results module 310 can be configured to display the positive or negative indicator in a variety of formats. For example, the results module 310 can cause the display of an indicator on the display itself, in a Microsoft Word® document, or in an Excel® spreadsheet. The results module 310 can also be configured to generate an external alert when a particular display is given a negative indicator (e.g., the results module 310 can be configured to send an e-mail alert to an administrator). While the results module 310 of computing system 300 can be configured to display the outcome of the screen display accessibility test other configurations are possible. For example, the screen display module 306 and/or the testing engine 308 can also display the outcome of the screen display accessibility test.

Figure 4:
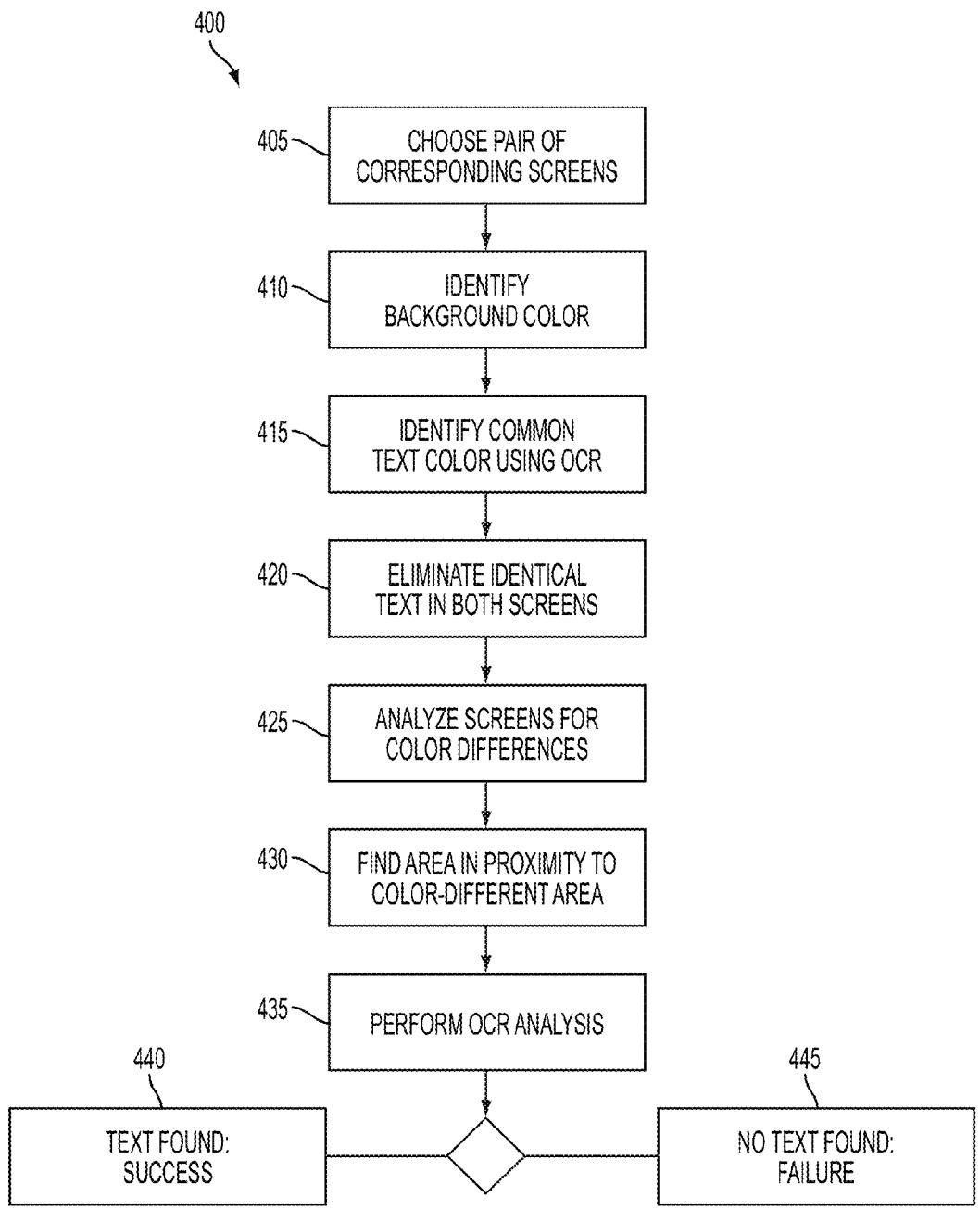
FIG. 4 is a block diagram of a method for use with the computer system of FIG. 3.

In operation, referring to FIG. 4, with further reference to FIGS. 1a-1d, 2a-2d, and 3, an exemplary process 400 is shown for testing for corresponding screens, and further testing the corresponding screens for color coded information and accessibility to colorblind people. An exemplary embodiment of process 400 uses the computing system 300 (although this is not required), and includes the steps set forth below. The process 400, however, is exemplary only and not limiting. The process 400 can be altered (e.g., by having stages added, removed, altered, or rearranged).

At step 405, the testing engine 308 can analyze a set of screens for two or more screens that correspond to each other. Corresponding screens can contain all, or almost all the same elements, including similar text, similar screen layouts, similar fields, similar content and similar functionality and similar graphics. Corresponding screens can also include different elements (e.g., different color coded information and/or different text associated with color coded information). For example, testing engine 308 can identify the following pairs or groups of corresponding screens: FIGS. 1a and 1b, FIGS. 1c and 1d, FIGS. 2a and 2b, FIGS. 2c and 2d, and FIGS. 7a, 7b and 7c. Other pairings or groupings of corresponding screens in the above identified figures are possible. The elements that the testing engine 308 can consider when analyzing how similar two or more screens are can be preset, configured by a user, and/or automatically extracted from the screens by analyzing which elements are common to the screens.

Further, the testing engine 308 can apply a similarity score to a set of screens, which can take into account various elements included in the set of screens, in order to analyze the similarity between screens. Each element to be considered can be assigned a specific weight in the total similarity score between screens. Further, the total similarity score between screens can be compared to a configurable threshold score to determine if the screens are similar. For example, two screens may be considered similar if they exceed a threshold total similarity score of 85%. In another example, a threshold similar score is not used and two screens from a defined set of screen displays that most resemble each other can be identified as corresponding screens. Further, in an exemplary embodiment, when analyzing the similarity between screen displays, the testing engine 308 can ignore certain areas of the screen (e.g., the testing engine 308 can ignore the header and footer portions of the screens and only analyze the body portions for similarity).

In another example, determining whether two screens correspond to one another can be accomplished by detecting similar patterns in a user's interactions with a screen display as a user navigates through multiple screen displays. A user's interactions can include, for example, mouse clicks and text entry, and can be logged for each screen display. To track which screens a user (or users) interacted with, each screen can have an identifier associated with it. When a user interaction pattern is detected on two or more screens (e.g., similar sequence of mouse clicks and/or text entry, similar locations of mouse clicks and/or text entry), then the testing engine can be configured to further test this set of screens for similar elements (e.g., similar text, similar screen layouts, similar fields, similar content, similar functionality and similar graphics). For example, a similar user interaction pattern might be detected for two screens if a user (or users), when using those two screens, inputs text into a field found in the upper right hand corner, then clicks in the middle of the screen to advance onward. Because a similar user interaction pattern was detected for both screens they are more likely to be corresponding screens, and the testing engine 308 can further compare them for similar elements, as described above, to determine whether they are indeed corresponding screens.

In yet another example, the testing engine can be combined with an automated screen display testing algorithm that creates a set of screen displays to test. Testing engine 308 can test for corresponding screens within the set of screen displays generated by the automated testing tool. Examples of existing automated screen display testing programs include EXSYST, which was developed as part of the Software-Cluster project EMERGENT, or GUITAR, originally developed by Atif Memon at the Event-Driven Software Lab, although other automated screen display testing programs may be used. In a further example, the testing engine 308 can test multiple instances of the same screen display for correspondence based on a user's interaction with the screen display. In still another example, a set of screen displays can be manually tested for correspondence by clicking through each screen display one by one.

At step 410, the testing engine 308 can be configured to identify the background color of corresponding screens. The background color can be defined as the color (besides the text color) within the entire screen display, or within a particular area of the screen display, which occurs most often in corresponding screens. Accordingly, the background color can be identified by analyzing the color code for each pixel on corresponding screens and determining the total number of pixels per color. The color code occurring in the most pixels can be characterized as the background color. Other algorithms to determine the background color are also possible. For example, the testing engine 308 can identify the color light gray as the background color for the corresponding screens shown in FIGS. 1*a* and 1*b*. In another example, the testing engine 308 can identify several background colors, each background color corresponding to an area where text is written. For example, in fields 110*a* and 110*b*, the testing engine 308 can identify gray as the background color for the text "Theology" and white as the background color for the text "Economics."

At step 415, the most common text color for corresponding screen displays can be identified. In some embodiments, optical character recognition (OCR) algorithms can be used to detect text areas in corresponding screen displays. Examples of existing OCR programs that can be used include OCRopus released under the Apache License, GNU Optical Character Recognition (GOCR), CuneiForm developed at Cognitive Technologies, GNU Ocrad, Tesseract OCR and OCRFeeder, although other OCR programs can be used. The color occurring most often in these text areas (besides the background color) can be considered the most common text color for the corresponding screen displays. For example, in FIGS. 2*a* and 2*b*, the most common text color is black. Other algorithms to determine the most common text color are also possible.

Figure 5A:
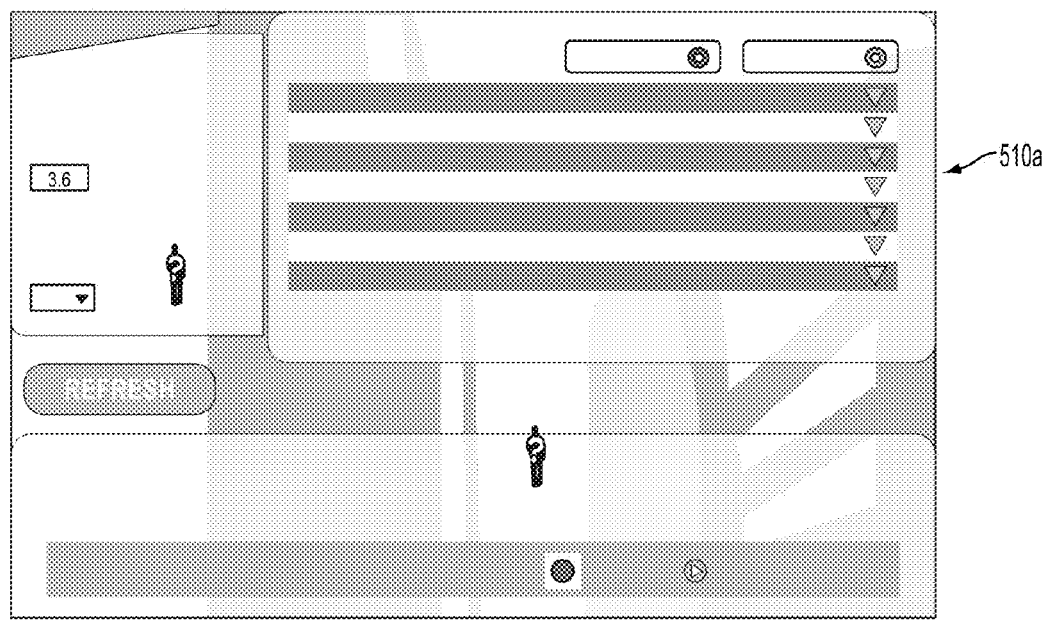
FIGS. 5a and 5b are exemplary results after applying an algorithm to remove or hide identical text in corresponding screen displays.
Figure 5B:
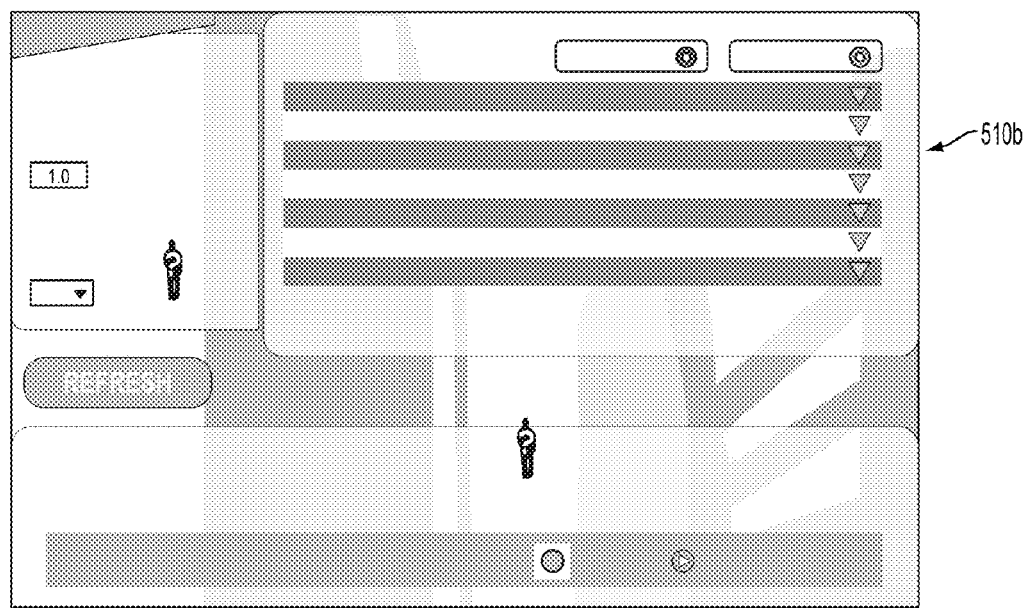

At step 420, the testing engine 308 can apply further OCR analysis to identify identical text between corresponding screen displays. For example, in FIGS. 1*a* and 1*b* identical text in fields 110*a* and 110*b* listing the different areas of study can be identified. Identical text can be removed from corresponding screen displays or can be hidden by converting the color of the identical text to the same color as the background color of corresponding screen displays. FIGS. 5*a* and 5*b* illustrate exemplary results of removing or hiding identical text from corresponding screens 100*a* and 100*b* found in FIGS. 1*a* and 1*b*. For example, because the different areas of study found in fields 110*a* and 110*b* of corresponding screens 100*a* and 100*b* are identical, the text was removed or hidden and no longer appears in fields 510*a* and 510*b* of FIGS. 5*a* and 5*b*. In some embodiments, the background color for the identical text may not be the same color as the general background color for the entire screen display. Accordingly, the color of the text may be converted to the same background color of the area within which the text is found.

At step 425, corresponding screens can be analyzed by the testing engine 308 for color differences. For example, the testing engine 308 can analyze the corresponding screens 100*a* and 100*b* illustrated in FIGS. 1*a* and 1*b*, and identify the red/green circles 120*a* and 120*b* as the only areas of color difference ("color-different area"). In another example, the testing engine 308 can analyze the corresponding screens 200*a* and 200*b* illustrated in FIG. 2*a* and FIG. 2*b*, and identify the colored bar indicators found in "Quality" fields 210*a* and 210*b* as the color-different areas. In some embodiments, the color-different areas can be an entire screen. For example, one screen of the corresponding screens can be entirely red, while the other screen of the corresponding screens can be entirely green.

Figure 6:
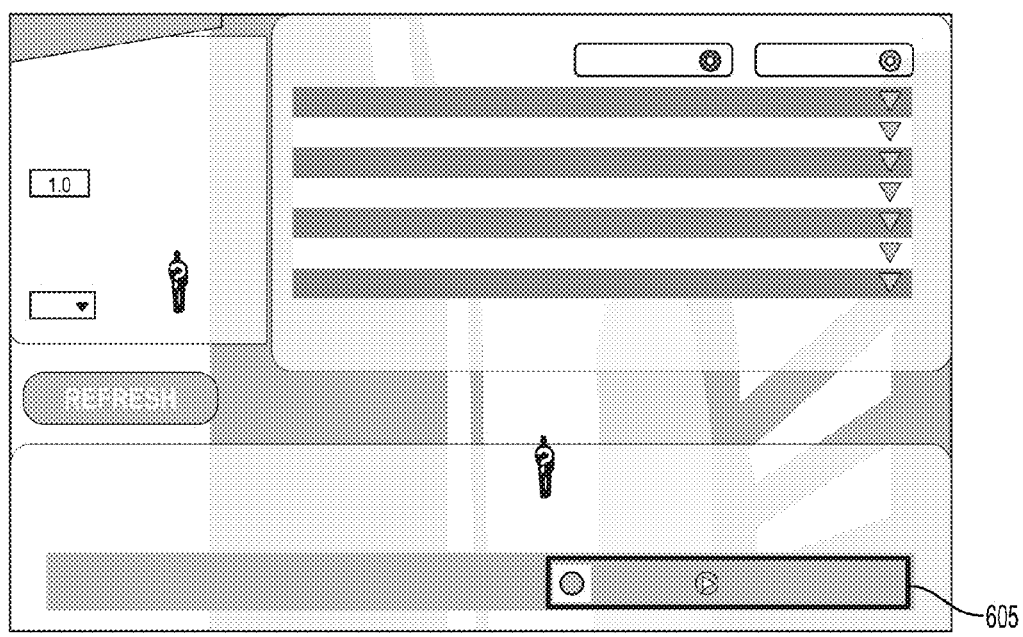
FIG. 6 illustrates an exemplary diagram of where text pertaining to color coded information can be expected to be found.

At step 430, the testing engine 308 can perform further OCR analysis in proximity to the identified color-different area to determine whether there is any text present in the corresponding screens that describes the color coded information. Proximity to the color-different area can be predefined and/or configured by a user. For example, in FIG. 6, the proximity to a color-different area is emphasized by the black box 605. For corresponding screen displays containing language that is written from left to right, any text that might describe the color coded information would typically appear to the right of the color different area (as shown in FIG. 6). In contrast, in screens containing language written from right to left, any text describing the color coded information commonly appears to the left of the color-different area. In some embodiments, the testing engine 308 can take into account the language of the text included in corresponding screens when determining the proximity to the color-different areas. In an embodiment where step 420 eliminates or hides identical text, any text that remains in proximity to the identified color-different area is likely to describe the color coded information.

In another embodiment, step 420 can be eliminated and an OCR analysis can be performed only in proximity to the identified color-different areas to determine whether there is any text present and whether any text detected in the identified color-different areas is identical or not. For example, the testing engine 308 can perform an OCR analysis on corresponding screens 100a and 100b (as illustrated in FIGS. 1a and 1b) in proximity to the red colored circle 120a and the green colored circle 120b and determine that there is no text present that describes the color coded information. In another example, the testing engine 308 can perform an OCR analysis on corresponding screens 200a and 200b (as illustrated in FIGS. 2a and 2b) in proximity to the colored bar indicators found in "Quality" fields 210a and 210b and determine that there is no text present that describes the color coded information. In contrast, the testing engine 308 can perform an OCR analysis on corresponding screens 200c and 200d (as illustrated in FIGS. 2c and 2d) in proximity to the colored bar indicators (e.g., "weak" or "strong" that appears to the right of the colored bar indicators) found in "Quality" fields 210c and 210d and determine that there is text present that describes the color coded information.

Figure 7A:
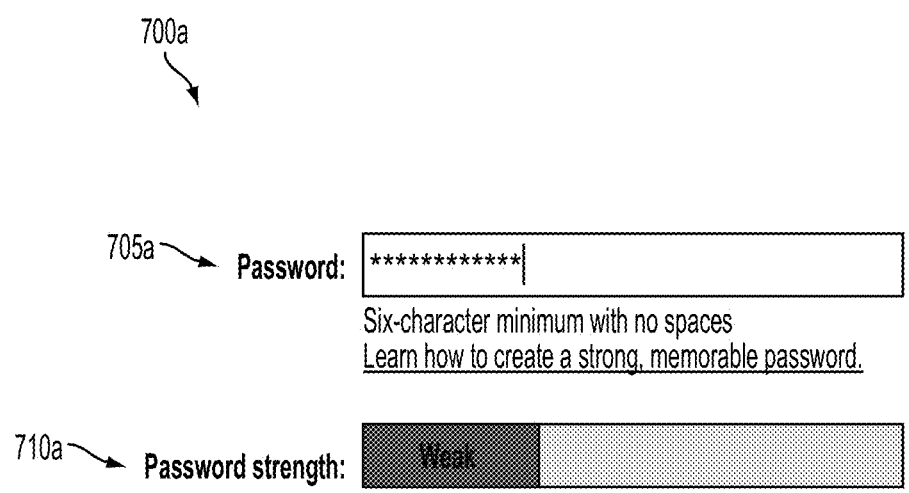
FIGS. 7a-7c are exemplary screen displays including color and text to convey information to a user.
Figure 7B:
Figure 7C:
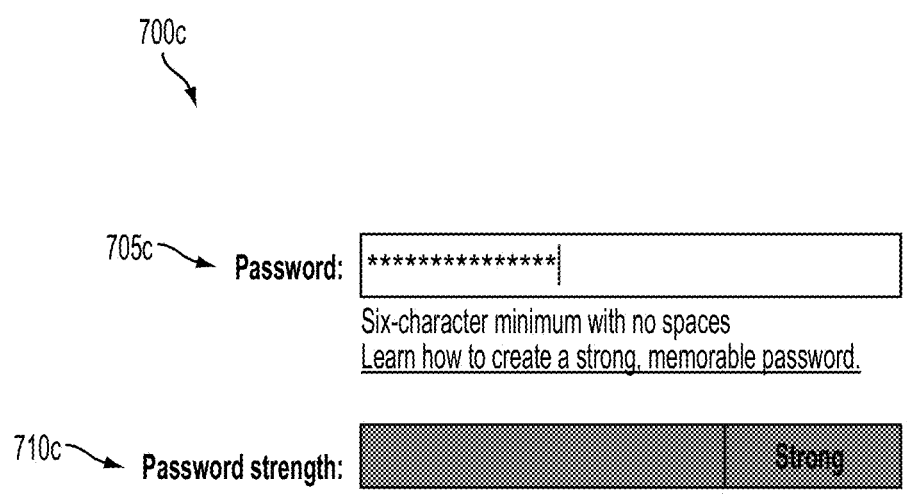

In another example, as shown in FIGS. 7a-7c, the text describing the color-different areas appears on the color-different areas themselves. FIGS. 7a-7c illustrate screens 700a-700c including fields 705a-705c for entering a password, and colored bar indicators 710a-710c, where the color of the bar indicator denotes the strength of the entered password. In addition, the colored bar indicators 710a-710c include text appearing on top of the bar indicators represent the information conveyed by the colored bars (e.g., red bar indicator 710a denotes a weak password, yellow bar indicator 710b denotes a medium strength password, and green bar indicator 710c denotes a strong password). The testing engine 308 can perform an OCR analysis on corresponding screens 700a, 700b and 700c in proximity to the colored bar indicators 710a, 710b and 710c and/or on the indicators 710a, 710b, and 710c themselves, and determine that there is text present that describes the color coded information.

At step 435, if the testing engine 308 detects that corresponding screens contain color coded information with no text at all, or no meaningful text, in proximity to or within the color-different areas, then the process 400 can continue to step 445, otherwise the process 400 can continue to step 440.

In some embodiments, in addition to, or in place of, performing an OCR analysis at step 435, the corresponding screens can be analyzed for color coded information that can be accessible to colorblind people even without including text. For example, a color-different area that appears as a vertical traffic light and displays a green light at the bottom of the traffic light can be accessible to colorblind people based on the position of the light (e.g., colorblind people expect that the color green will appear at the bottom of a vertical traffic light even if they cannot discern the actual color). Accordingly, the testing engine 308 can compare the color-different areas of corresponding screens to a set of figures familiar to colorblind people (e.g., a vertical traffic light, an octagonal stop sign). If the testing engine 308 determines that the color-different areas are accessible to colorblind people even without including any text, then the testing engine 308 can further determine that the corresponding screens passed the color accessibility test and provide a related indicator.

At step 440, if meaningful text is detected adjacent to or within the color-different areas of the corresponding screen displays, then the testing engine 308 can determine at step 440 that the corresponding screens passed the colorblind accessibility test. For example, the testing engine 308 can determine that corresponding screens 200c and 200d passed the color accessibility test and provide a corresponding indicator. Likewise, the testing engine 308 can determine that corresponding screens 700a, 700b and 700c, in FIGS. 7a, 7b and 7c passed the color accessibility test and provide a corresponding indicator.

At step 445, the testing engine 308 can determine that the corresponding screens failed the color accessibility test. For example, the testing engine 308 can determine that screens 100a and 100b in FIGS. 1a and 1b failed the color accessibility test. In another example, the testing engine 308 can determine that screens 200a and 200b failed the color accessibility test. In some embodiments, if the colorblind accessibility test fails, the testing engine 308 can automatically add text to the color coded information to make the information accessible to colorblind individuals. For example, an editing unit can be included in computing system 300 to allow a user to manually input text within or adjacent to the color coded information. In some embodiments, if the colorblind accessibility test fails, the testing engine can send an alert of the failure (e.g., via email, short messaging service (SMS) and/or push notification) according to predefined alert preferences.

At steps 440 and/or 445, the testing engine 308 can transmit/display the results of the test directly to the user, or can display/transmit the results of the test indirectly, for example, via the screen display module 306 or the results module 310. The results of the test can appear on the screen display itself, or in some other format, for example in a Microsoft Word® document or Excel® spreadsheet. In some embodiments, the testing engine can send the results of the test to a user (e.g., via email, short messaging service (SMS) and/or push notification) according to predefined user preferences.

The process 400 described in FIG. 4 can be applied manually to a set of screens or can be combined with an automated screen display testing algorithm to test each one of a sequence of screen displays automatically. Each screen display that is tested can be annotated with the result of the colorblind accessibility test and saved. Further, a list of screens failing and/or passing the colorblind accessibility test, discussed above in connection with FIG. 4, can be generated, for example in a Microsoft Word® document or Excel® spreadsheet. Additionally, a human may test the screens appearing on the list for false positive results. In a further embodiment, the results of the colorblind accessibility test for the sequence of screen displays tested via an automated screen display testing program can be recorded using standard screen capture software.

Figure 8:
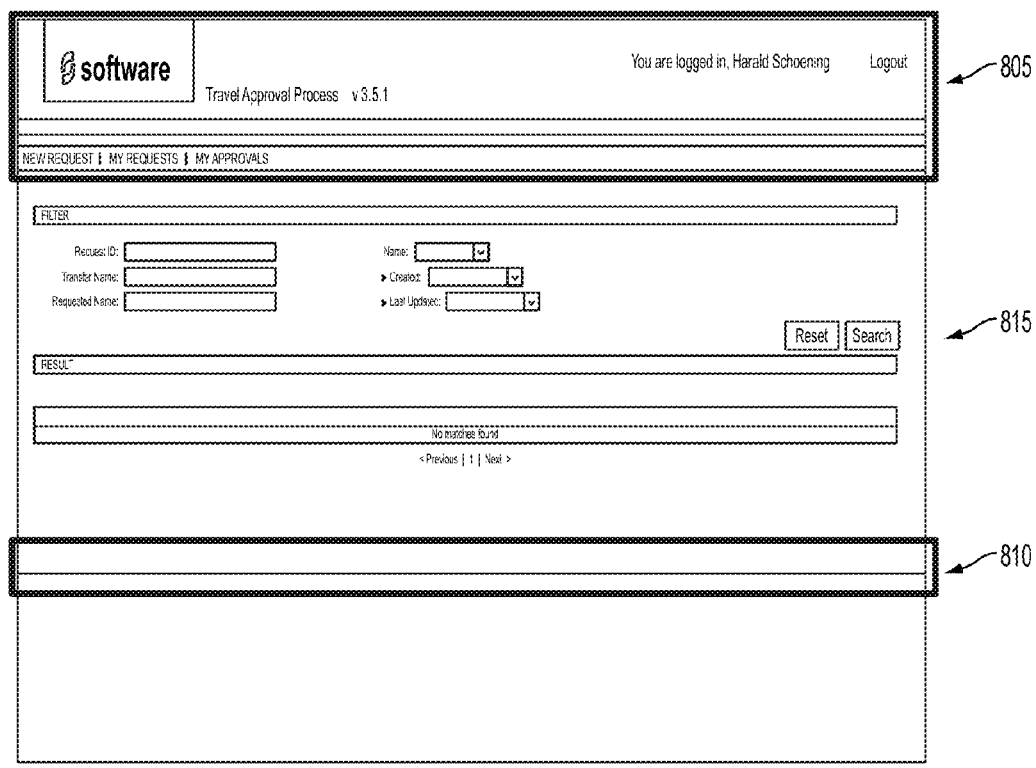
FIG. 8 is an exemplary structure of a screen display.

Referring to FIG. 8, exemplary screen structures analyzed herein can include simple graphical elements and text, which form various screen display areas, e.g., a header 805, a footer 810, and a body 815. Process 400 for testing corresponding screens for colorblind accessibility can be applied to the entire screen display or to portions thereof. For example, the process 400 can be applied to one or more portions of the screen at a time, testing each portion(s) separately. The areas to be tested can be defined manually before the test is executed and/or can be extracted from a sequence of screens, for example, obtained by an automated screen display testing tool.

The subject matter described herein can be implemented in digital electronic circuitry, or in computer software, firmware, or hardware, including the structural means disclosed in this specification and structural equivalents thereof, or in combinations of them. The subject matter described herein can be implemented as one or more computer program products, such as one or more computer programs tangibly embodied in an information carrier (e.g., in a machine-readable storage device), or embodied in a propagated signal, for execution by, or to control the operation of, data processing apparatus (e.g., a programmable processor, a computer, or multiple computers). A computer program (also known as a program, software, software application, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file. A program can be stored in a portion of a file that holds other programs or data, in a single file dedicated to the program in question, or in multiple coordinated files (e.g., files that store one or more modules, subprograms, or portions of code). A computer program can be deployed to be executed on one computer or on multiple computers at one site or distributed across multiple sites and interconnected by a communication network.

The processes and logic flows described in this specification, including the method steps of the subject matter described herein, can be performed by one or more programmable processors executing one or more computer programs to perform functions of the subject matter described herein by operating on input data and generating output. The processes and logic flows can also be performed by, and apparatus of the subject matter described herein can be implemented as, special purpose logic circuitry, e.g., an FPGA (field programmable gate array) or an ASIC (application-specific integrated circuit).

Processors (sometimes referred to herein as a server) suitable for the execution of a computer program include, by way of example, both general and special purpose microprocessors, and any one or more processor of any kind of digital computer. Generally, a processor will receive instructions and data from a read-only memory or a random access memory or both. The essential elements of a computer are a processor for executing instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. Information carriers suitable for embodying computer program instructions and data include all forms of non-volatile memory, including by way of example semiconductor memory devices, (e.g., EPROM, EEPROM, and flash memory devices); magnetic disks, (e.g., internal hard disks or removable disks); magneto-optical disks; and optical disks (e.g., CD and DVD disks). The processor and the memory can be supplemented by, or incorporated in, special purpose logic circuitry.

To provide for interaction with a user, the subject matter described herein can be implemented on a computer (e.g., a mobile communication device) having a display device (e.g., a liquid crystal display), for displaying information to the user and a keypad by which the user can provide input to the computer. Other kinds of devices can be used to provide for interaction with a user as well. For example, feedback provided to the user can be any form of sensory feedback, (e.g., visual feedback, auditory feedback, or tactile feedback), and input from the user can be received in any form, including acoustic, speech, or tactile input.

The subject matter described herein can be implemented in a computing system that includes a back-end component (e.g., a data server), a middleware component (e.g., an application server), or a front-end component (e.g., a client computer having a graphical user interface or a web browser through which a user can interact with an implementation of the subject matter described herein), or any combination of such back-end, middleware, and front-end components. The components of the system can be interconnected by any form or medium of digital data communication, e.g., a communication network. Examples of communication networks include a local area network ("LAN") and a wide area network ("WAN"), e.g., the Internet.

The description herein describes network elements, computers, and/or components of a system used to implement embodiments of the disclosed subject matter that can include one or more modules. As used herein, the term "module" is understood to refer to computing software, firmware, hardware, and/or various combinations thereof. Modules, however, are not to be interpreted as software that is not implemented on hardware, firmware, or recorded on a non-transitory processor readable recordable storage medium (i.e., modules are not software per se). It is noted that the modules are exemplary and include at least some physical, tangible hardware. The modules can be combined, integrated, separated, and/or duplicated to support various applications. Also, a function described herein as being performed at a particular module can be performed at one or more other modules and/or by one or more other devices instead of or in addition to the function performed at the particular module. Further, the modules can be implemented across multiple devices and/or other components local or remote to one another. Additionally, the modules can be moved from one device and added to another device, and/or can be included in both devices.

Other embodiments are within the scope and spirit of the disclosed subject matter.

What is claimed is:

1. A non-transitory computer readable medium comprising instructions that, when executed by a computer, cause the computer to:

receive data corresponding to a plurality of screen displays including information encoded in color;

identify first and second corresponding screen displays from the plurality of screen displays;

detect whether any text is different in the first and second corresponding screen displays at a first location;

detect color encoded information that is different in the first and second corresponding screen displays at a second location;

determine a proximity of the first and the second locations when there is text that is different in the first and second corresponding screen displays at the first location by determining whether the first location is located at least partially within the second location, and when the first location is not located at least partially within the second location, determining whether the first location is located within a predetermined distance of the second location;

generate a positive colorblindness accessibility indicator when the first location is located at least partially within the second location or within the predetermined distance of the second location; and generate a negative colorblindness accessibility indicator when the first location is not located at least partially within the second location or within the predetermined distance of the second location.

2. The computer readable medium of claim 1, wherein the color encoded information varies based on at least one of i) a user input, ii) a numerical value, and iii) an external system value.

3. The computer readable medium of claim 1, wherein the instructions are further configured to cause the computer to detect text that is different in the first and second corresponding screen displays by:

detecting identical text in the first and second corresponding screen displays; and at least one of i) deleting the identical text from the first and the second corresponding displays, and ii) changing a color of identical text to match a background color.

4. The computer readable medium of claim 1, wherein the first and second corresponding screen displays are at least one of:

two instances of the same screen at different points in time;

two instances of the same screen with different input from a single user;

two instances of the same screen with different input from two users; and two instances of the same screen with different input from an external system.

5. The computer readable medium of claim 1, wherein the instructions are further configured to cause the computer to identify the first and second corresponding screen displays as a function of at least one of: i) a layout of the first and second corresponding screens, ii) fields in the first and second corresponding screens, iii) text in the first and second corresponding screens, and iv) graphics in the first and second corresponding screens.

6. The computer readable medium of claim 1, wherein the instructions are further configured to cause the computer to detect the color encoded information that is different only in a selected portion of the corresponding screen displays.

7. A computer implemented method comprising:

receiving, at a processor, data corresponding to a plurality of screen displays including information encoded in color;

identifying first and second corresponding screen displays from the plurality of screen displays using the processor;

detecting whether any text is different in the first and second corresponding screen displays at a first location using the processor;

detecting color encoded information that is different in the first and second corresponding screen displays at a second location using the processor;

determining a proximity of the first and the second locations using the processor when there is text that is different in the first and second corresponding screen displays at the first location by determining whether the first location is located at least partially within the second location, and when the first location is not located at least partially within the second location, determining whether the first location is located within a predetermined distance of the second location;

generating a positive colorblindness accessibility indicator, using the processor, when the first location is located at least partially within the second location or within the predetermined distance of the second location; and generating a negative colorblindness accessibility indicator, using the processor, when the first location is not located at least partially within the second location or within the predetermined distance of the second location.

8. The method of claim 7, wherein the color encoded information varies based on at least one of i) a user input, ii) a numerical value, and iii) an external system value.

9. The method of claim 7, wherein detecting text that is different in the first and second corresponding screen displays further comprises:

detecting identical text in the first and second corresponding screen displays; and at least one of i) deleting the identical text from the first and the second corresponding displays, and ii) changing a color of identical text to match a background color.

10. The method of claim 7, wherein the first and second corresponding screen displays are at least one of:

two instances of the same screen at different points in time;

two instances of the same screen with different input from a single user;

two instances of the same screen with different input from two users; and two instances of the same screen with different input from an external system.

11. The method of claim 7, wherein identifying the first and second corresponding screen displays is a function of at least one of: i) a layout of the first and second corresponding screens, ii) fields in the first and second corresponding screens, iii) text in the first and second corresponding screens, and iv) graphics in the first and second corresponding screens.

12. The method of claim 7, wherein detecting color encoded information that is different occurs only in a selected portion of the corresponding screen displays.

13. An apparatus comprising:

a screen display module configured to receive data corresponding to a plurality of screen displays including information encoded in color;

an identification module configured to identify first and second corresponding screen displays from the plurality of screen displays;

a detection module configured to detect whether any text is different in the first and second corresponding screen displays at a first location and to detect color encoded information that is different in the first and second corresponding screen displays at a second location;

a proximity module configured to determine a proximity of the first and the second locations when there is text that is different in the first and second corresponding displays at the first location by determining whether the first location is located at least partially within the second location, and when the first location is not located at least partially within the second location, determining whether the first location is located within a predetermined distance of the second location; and an output module configured to generate a positive colorblindness accessibility indicator when the first location is located at least partially within the second location or within the predetermined distance of the second location and to generate a negative colorblindness accessibility indicator when the first location is not located at least partially within the second location or within the predetermined distance of the second location.

14. The apparatus of claim 13, wherein the color encoded information varies based on at least one of i) a user input, ii) a numerical value, and iii) an external system value.

15. The apparatus of claim 13, wherein the detection module is further configured to detect text that is different in the first and second corresponding screen displays by:
   detecting identical text in the first and second corresponding screen displays; and
   at least one of i) deleting the identical text from the first and the second corresponding displays, and ii) changing a color of identical text to match a background color.

16. The apparatus of claim 13, wherein the first and second corresponding screen displays are at least one of:
   two instances of the same screen at different points in time;
   two instances of the same screen with different input from a single user;
   two instances of the same screen with different input from two users; and
   two instances of the same screen with different input from an external system.

17. The apparatus of claim 13, wherein the identification module is further configured to identify the first and second corresponding screen displays as a function of at least one of: i) a layout of the first and second corresponding screens, ii) fields in the first and second corresponding screens, iii) text in the first and second corresponding screens, and iv) graphics in the first and second corresponding screens.

18. The apparatus of claim 13, wherein the detection module is further configured to detect the color encoded information that is different only in a selected portion of the corresponding screen displays.

* * * * *